United States Patent [19]

Koike et al.

[11] Patent Number: 5,369,038

[45] Date of Patent: Nov. 29, 1994

[54] METHOD FOR IMMUNOLOGICAL ASSAY OF FREE LIPOPROTEIN ASSOCIATED COAGULATION INHIBITOR (LACI) AND KIT THEREFOR

[75] Inventors: Yukiya Koike, Hino; Koji Suzuki, Tsu; Yataro Ichikawa, Tokorozawa, all of Japan

[73] Assignee: Teijin Limited, Osaka, Japan

[21] Appl. No.: 969,368

[22] Filed: Oct. 30, 1992

[30] Foreign Application Priority Data

Oct. 31, 1991 [JP] Japan ................................ 3-311442
Nov. 29, 1991 [JP] Japan ................................ 3-339560

[51] Int. Cl.$^5$ ...................... G01N 33/53; C12Q 1/00; C07K 15/28
[52] U.S. Cl. .................................. 436/548; 435/7.1; 435/7.94; 435/975; 530/388.25
[58] Field of Search ................ 435/7.4, 810, 7.94, 435/7.1, 975, 240.27; 530/388.25; 436/548

[56] References Cited

PUBLICATIONS

Rapaport, S. I.; Blood 73:359-365 (1989).
Nordfang, O. et al.; Biochemistry 30:10,371-10,376 (1991).
Broze, G. J. et al.; Biochemistry 29:7539-7546 (1990).
Blood, vol. 72, No. 6, Dec. 1988, W. F. Novotny et al. "Platelets Secrete a Coagulation Inhibitor Functionally and Antigenically Similar to the Lipoprotein Associated Coagulation Inhibitor." pp. 2020-2025.
Nature, vol. 338, Apr. 6, 1989, pp. 518-520 Thomas J. Girard et al. "Functional Significance of the Kunitz-Type Inhibitory Domains of Lipoprotein-Associated Coagulation Inhibitor."
Journal of Biological Chemistry. (Microfilms) vol. 263, No. 13, May 5, 1988, Baltimore Md. US Tze-Chein Wun et al. "Cloning and Characterization of a cDNA Coding for the Lipoprotein-Associated Coagulation Inhibitor Shows That it Consists of the Three Tandem Kunitz-Type Inhibitory Domains."
Journal of Biological Chemistry. (Microfilms) vol. 264, No. 31, Nov. 5, 1989, Baltimore Md. US, pp. 18832-18837 W. F. Novotny et al. "Purification and Characterization of the Lipoprotein-Associated Coagulation Inhibitor from Human Plasma."

*Primary Examiner*—Robert A. Wax
*Assistant Examiner*—Eric Grimes
*Attorney, Agent, or Firm*—Wenderoth, Lind & Ponack

[57] ABSTRACT

In methods for immunologically assaying free lipoprotein associated coagulation inhibitor (hereafter abbreviated as "LACI") in a human inspection sample using a first antibody immobilized on an insoluble carrier and a labeled second antibody, a method for immunological assay of free LACI and a kit therefor wherein (i) any one antibody of the first antibody and the second antibody is a monoclonal antibody recognizing the polypeptide (K3) of the following amino sequence Leu Thr Pro Ala Asp Arg Gly Leu Cys Arg
Ala Asn Glu Asn Arg Phe Tyr Tyr Asn Ser
Val (hereafter referred to as a "K3-antibody"), and
(ii) the other antibody is a monoclonal antibody recognizing the polypeptide (K1) of the following amino acid sequence Ala Phe Lys Ala Asp Asp
Gly Pro Cys Lys Ala Ile
Met Lys Arg Phe Phe Phe
Asn Ile Phe (hereafter referred to as a "K1-antibody").

11 Claims, 3 Drawing Sheets

| Antibody / Standard curve | First antibody (Immobilized antibody) | Second antibody (Enzyme-labeled antibody) |
|---|---|---|
| 1 | K3 - antibody | K1 - antibody |
| 2 | K3 - antibody | K2 - antibody | ately assaying free lipoprotein-associated coagulation inhibitor in a human inspection sample in high sensitivity, and a kit therefor.

METHOD FOR IMMUNOLOGICAL ASSAY OF FREE LIPOPROTEIN ASSOCIATED COAGULATION INHIBITOR (LACI) AND KIT THEREFOR

DETAILED DESCRIPTION OF THE INVENTION

Industrially Applicable Field

This invention relates to immunological assay of free lipoprotein-associated coagulation inhibitor in a human inspection sample. More specifically, this invention relates to a method for assaying lipoprotein-associated coagulation inhibitor in a free state in a human inspection sample in high sensitivity, and a kit therefor.

In this specification, the term "LACI" means lipoprotein-associated coagulation inhibitor.

"free LACI" means LACI not associated with lipoprotein or other proteins.

LACI is also designated extrinsic pathway inhibitor (EPI) or tissue factor pathway inhibitor (TFPI).

Prior Art

Extrinsic blood coagulation is started by contact of the blood with tissue thromboplastin (herein after referred to as tissue factor (TF)). Tissue factor (TF) is a membrane protein having a molecular weight of 58,000 and exists in many tissues, particularly in the brain and the placenta. By contact with TF, Factor VII or its active form factor VIIa Forms a complex with TF, and factor X is proteolytically activated into factor Xa, and thereby the coagulation system starts.

In the course of researches so far made on adjustment of extrinsic blood coagulation started by TF, it was made clear that when TF is incubated with serum, its in vitro activity is inhibited. At least one of these factors is defined as extrinsic pathway inhibitor (EPI) or lipoprotein-associated coagulation inhibitor (LACI).

Tissue factor inhibitory activity by LACI means an activity to inhibit start of blood coagulation by the TF-VIIa complex.

Broze et al. disclosed that Hep G2 cells (human hepatoma cell line) secreted an inhibiting factor having the same characteristics as EPI existing in the serum (plasma) (Broze et al.; Blood, 69, 150–155 (1987)). Further, as for LACI, its amino acid sequence consisting of 276 amino acid residues and its secondary structure are disclosed also by Broze et al. in Nature, 338, 518–520 (1989).

According to the above Nature, it is reported that LACI has three Kunitz domains, and the first Kunitz domain from the N-terminus is the binding site to TF-VIIa complex and the second Kunitz domain therefrom is the binding site to factor Xa, but it is reported that the third Kunitz domain has no function. Further in this Nature, there is no disclosure about assay of free LACI in the blood and the meaning of the assay.

Problems to be Solved by the Invention

Thus the present inventors further studied on free LACI in the blood and its assay.

Part of LACI in the blood exists in such a form that it is binding to lipoproteins such as LDL (low density lipoprotein), but the other part exists as free LACI and the free LACI is considered to take part deeply in inhibition of thrombus formation. Particularly in thrombotic diseases such as pulmonary thrombus wherein microthrombi are formed in the blood vessels, $\alpha_2$PI ($\alpha_2$-plasmin inhibitor), fibrinogen, etc. have so far been known as indicator substances monitoring the conditions of the disease, but it was recently reported that these substances did not change in correspondence to the change of the state of the disease. Therefore, it has been desired to find a new indicator whereby change of the state of the above thrombotic diseases can exactly be monitored.

On the other hand, the present inventors had an eye to the third Kunitz domain from the N-terminus, synthesized part of the polypeptide, prepared a monoclonal antibody specifically recognizing the polypeptide, and further continued their studies on inhibition of binding of LDL (human LDL, Sigma Co.) to LACI. As a result, it was found that the third Kunitz domain of LACI is a binding site of LDL (low density lipoprotein). Then, by utilizing the characteristic of the above monoclonal antibody to inhibit binding between LACI and LDL, a system could be drawn up to be capable of selectively and exactly assaying free LACI (LACI not binding to LDL) in the blood. Further, it was found that this assay system is useful for diagnosis of thrombotic diseases wherein microthrombi are formed in the living bodies.

Means for Solving the Problems

This invention was accomplished based on the above findings, and is a method for immunologically assaying free lipoprotein-associated coagulation inhibitor (hereinafter abbreviated as "LACI") in a human inspection sample using a first antibody immobilized on an insoluble carrier and a labeled second antibody, wherein (i) any one antibody of the first antibody and the second antibody is a monoclonal antibody recognizing the polypeptide (K3) of the following amino acid sequence Leu Thr Pro Ala Asp Arg Gly Leu Cys Arg
Ala Asn Glu Asn Arg Phe Tyr Tyr Asn Ser
Val (SEQ ID NO:1)(hereinafter referred to as a "K3-antibody"), and (ii) the other antibody is a monoclonal antibody recognizing the polypeptide (K1) of the following amino acid sequence Ala Phe Lys Ala Asp Asp Gly Pro Cys Lys
Ala Ile Met Lys Arg Phe Phe Phe Asn Ile
Phe SEQ ID NO:2)(hereinafter referred to as a "K1-antibody").

Further, according to this invention is provided a kit for immunologically assaying free lipoprotein-associated coagulation inhibitor (hereinafter abbreviated as "LACI") in a human inspection sample, which comprises a combination of (1) a first antibody immobilized on an insoluble carrier,
(2) a labeled second antibody,
(3) a solubilizing agent,
(4) a washing agent and
(5) in case of the labeling substance being an enzyme, a substrate for measuring the enzyme activity and a reaction-stopping agent, and wherein
  (i) any one antibody of the first antibody and the second antibody is a K3-antibody, and
  (ii) the other antibody is a K1-antibody.

This invention is described in more detail below.

In this specification, amino acid sequences are abbreviated in accordance with the method adopted by the IUPAC-IUB Committee of Biochemistry (CBN) and, for example, the following abbreviations are used.

| | |
|---|---|
| Ala | L-alanine |
| Arg | L-arginine |
| Asn | L-asparagine |
| Asp | L-aspartic acid |
| Cys | L-cysteine |
| Gln | L-glutamine |
| Glu | L-glutamic acid |
| Gly | glycine |
| His | L-histidine |
| Ile | L-isoleucine |
| Leu | L-leucine |
| Lys | L-lysine |
| Met | L-methionine |
| Phe | L-phenylalanine |
| Pro | L-proline |
| Ser | L-serine |
| Thr | L-threonine |
| Trp | L-tryptophan |
| Tyr | L-tyrosine |
| Val | L-valine |

[I] MONOCLONAL ANTIBODIES AND PREPARATION THEREOF

The present inventors synthesized polypeptides having the following three kinds of amino acid sequences and prepared monoclonal antibodies using them as antigens. The specific method is described below.

A. Antigen

Synthetic polypeptides (K1, K2 and K3) having the following three kinds of amino acid sequences are used as antigens.

Polypeptide K1
Ala Phe Lys Ala Asp Asp Gly Pro Cys Lys
Ala Ile Met Lys Arg Phe Phe Phe Asn Ile
Phe Polypeptide K2
Phe Leu Glu Glu Asp Pro Gly Ile Cys Arg
Gly Tyr Ile Thr Arg Tyr Phe Tyr Asn Asn
Gln  (SEQ ID NO: 3)

polypeptide K3
Leu Thr Pro Ala Asp Arg Gly Leu Cys Arg
Ala Asn Glu Asn Arg Phe Tyr Tyr Asn Ser
Val It is preferred that such a polypeptide is used as an antigen in such a form that it is bound to a carrier protein such as, for example, KLH (keyhole limpet hemocyanin).

B. Immunization of a Mouse with the Above Antigen

It is possible to use a female Balb/c mouse, but it is also possible to use a mouse of another strain. In this occasion, immunization plan and concentration of the antigen should be selected so that lymphocytes which received an adequate amount of antigen stimulation are formed. For example, after a mouse is intraperitoneally immunized with 50 µg of the antigen three times at intervals of two weeks, 30 µg thereof is further intravenously administered. Spleen cells are taken out several days after the final immunization for fusion.

C. Cell Fusion

The spleen of the immunized mouse is aseptically taken out, as is mentioned above, and unicellular suspensions are prepared therefrom. These spleen cells are cell-fused with mouse myeloma cells from a suitable line using a suitable fusion accelerator. The preferred ratio of the spleen cells to the myeloma cells is in the range of about 20:1–about 2:1. Use of 0.5–1.5 ml of the fusion medium per about $10^8$ spleen cells is appropriate.

Mouse myeloma cells used for cell fusion are well known, and in this invention is preferred P3-X63-Ag8-U1 cell (P3-U1) [refer to Yelton, D. F. et al., Current Topics in Microbiology and Immunology, 81, 1(1978)].

It is possible to use advantageously, for example, polyethylene glycol having an average molecular weight of 1000–4000 as a preferred fusion accelerator, but it is also possible to use other fusion accelerators known in this field.

D. Selection of Fused Cells

The mixtures of nonfused spleen cells, nonfused mouse myeloma cells and fused hybridoma cells are diluted with a selected medium not supporting nonfused mouse myeloma cells in separate vessels (for example, a microtiter plate), respectively, and the dilutions are subjected to culture for a time enough to make the nonfused cells die out (about 1 week). As the medium is used one which does not support the drug-resistant (for example, 8-azaguanine-resistant) and the nonfused mouse myeloma cells, (for example, HAT medium). In this selective medium, the nonfused myeloma cells die out. The nonfused spleen cells are nontumor cells and die out after a definite term (1 week later). Contrary to them, the fused cells possess tumor properties of myeloma parent cells and properties of parent spleen cells together, and can be alive in the selective medium.

E. Confirmation of an Antibody in Each Vessel

Thus, after hybridoma cells are detected, their culture supernatants are recovered, and screened for an antibody against the above-mentioned synthetic peptide of the formula [I] according to an enzyme linked immunosorbent assay. The supernatants which were found to be positive are checked for a property binding to LACI.

F. Cloning of Hybridoma Cells Producing a Desired Antibody

After hybridoma cells producing a desired antibody are cloned by a suitable process (for example, a limiting dilution method), the antibody can be produced by two different, in vitro or in vivo, processes. According to the first process, the monoclonal antibody can be obtained by culturing the hybridoma cells in a suitable medium for a certain time and recovering the monoclonal antibody produced by the hybridoma cells from the culture supernatant. According to the second process, the hybridoma cells can be intraperitoneally injected into a mouse possessing an isogenic gene or a semi-isogenic gene. The monoclonal antibody produced by the hybridoma cells can be obtained from the blood and ascites of the host animal after a certain time.

[II] IMMUNOLOGICAL ASSAY

II-(1) Monoclonal Antibodies

In assay of free LACI in a human inspection sample in this invention are used in combination a monoclonal antibody having a specific recognition site to the aforesaid amino acid sequence (K3) (K3-antibody) and a monoclonal antibody having a specific recognition site to the aforesaid amino acid sequence (K1) (K1-antibody).

It is difficult to assay free LACI in high sensitivity using a monoclonal antibody having a specific recognition site to the aforesaid amino acid sequence (K2) (K2-antibody) even in combination with a K3-antibody or even in combination with a K1-antibody.

Each of a K3-antibody and a K1-antibody used may be an intact antibody or may be Fab or F(ab')$_2$.

Further, the first antibody immobilized on the insoluble carrier may either a K3-antibody or a K1-antibody, but a preferred result is obtained by the combination that the first antibody is a K3-antibody and the labeled antibody is a K1-antibody.

II-(2) Human Inspection Sample

As a sample being the object of assay of free LACI in this invention, any human body fluid can be used so long as it may contain free LACI. Generally, serum, plasma, urine or an equivalent thereof can be used, and particularly plasma is preferably used.

II-(3) Assay Means

Assay of free LACI in this invention can be carried out by an immunological assay method well known per se (namely, sandwich method) so long as it uses the aforesaid K3-antibody and K1-antibody. The method may either be a one step method or a two step method.

Namely, either of the K3-antibody and the K1-antibody is immobilized on a suitable insoluble carrier. Then, the surface of the insoluble carrier is coated with a suitable substance (for example, bovine serum albumin) so as to avoid nonspecific binding between the insoluble carrier and the inspection sample to be assayed. The thus obtained insoluble carrier on which the first antibody was immobilized is contacted with a human inspection sample at a constant temperature for a constant time to carry out reaction. Thereby free LACI binds to the first antibody. Then after washing with a suitable washing agent, a solution of the second antibody labeled with a suitable labeling substance (for example, an enzyme) is contacted with the free LACI bound to the first antibody in the insoluble carrier at a constant temperature for a constant time to carry out reaction. The resultant insoluble carrier is washed with a suitable washing agent, and then is assayed the amount of the labeling substance of the second antibody (labeled antibody) bound onto the insoluble carrier.

The above-mentioned two step method can be replaced by a one step method. Namely, the one step method can be carried out by simultaneously mixing the first antibody immobilized on an insoluble carrier, the labeled second antibody and the human inspection sample, reacting them at a constant temperature for a constant time, and then assaying the amount of the labeling substance.

[III] Immunological Assay Kit

The kit of this invention for assay of free LACI is composed based on a combination of reagents in a usual sandwich method except (i), (ii), that
(i) either one antibody of the first antibody and the second antibody is a K3-antibody, and
(ii) the other antibody is a K1-antibody.

Namely, the immunological assay kit of this invention comprises
(1) a first antibody immobilized on an insoluble carrier,
(2) a labeled second antibody,
(3) a solubilizing agent
(4) a washing agent and
(5) in case of the labeling substance being an enzyme, a substrate for assaying the enzyme activity and a reaction-stopping agent.

As insoluble carriers, there can be exemplified macromolecules such as, for example, polystyrene, polyethylene, polypropylene, polyesters, polyacrylonitrile, fluororesins, crosslinked dextran and polysaccharides, and further paper, glass, metals and agarose, and a combination thereof, etc.

Further, shapes of the insoluble carrier can be various shapes such as, for example, tray shapes, spherical shapes, fibrous shapes, stick shapes, board shapes, vessel shapes, cells and test tubes.

Further, it is advantageous to use, as the labeling substances of the labeled antibodies, enzymes, fluorescent substances, self-luminous substances, radioactive substances, etc. There can be used peroxidases, alkaline phosphatases, $\beta$-D-galactosidase, etc. as enzymes; fluoresceine isothiocyanate, phycobili proteins, etc. as fluorescent substances; isolucinol, lucigenin, etc. as self-luminous substances; and $^{125}$I, $^{131}$I, $^{14}$C, $^{3}$H, etc. as radioactive substances. However, the labeling substances are not limited to those exemplified, and others ones can be used so long as they can be used in immunological assay methods.

When the labeling substance is an enzyme, a substrate and, if necessary, a color former are used for assay of its activity.

In case a peroxidase is used as the enzyme, as the substrate is used $H_2O_2$ and as the color former is used 2,2'-azinodi-[3-ethylbenzothiazolinesulfonic acid] ammonium salt (ABTS), 5-aminosalicylic acid, o-phenylenediamine, 4-aminoantipyrin, 3,3',5,5'-tetramethylbenzidine or the like; and in case an alkaline phosphatase is used as the enzyme, as the substrate is used o-nitrophenyl phosphate or the like; and in case $\beta$-D-galactosidase is used as the enzyme, as the substrate is used fluoresceine-di-($\beta$-D-galactopyranoside), 4-methylumbelliferyl-$\beta$-D-galactopyranoside or the like.

The solubilizing agent of (3) in the kit for the aforesaid immunological assay can be one usually used for immunological assay, and suitable examples thereof are those having a pH in the range of 6.0 to 8.0, including such as, for example, phosphate buffers, Tris hydrochloride buffers and acetate buffers. Further, similarly, as the washing agent of (4), one generally used in immunological assay is used as such. Examples thereof are physiological saline, phosphate buffers, Tris hydrochloride buffers and their mixed solutions. It is possible to add to such a washing agent a nonionic surfactant such as Triton X 100, Tween 20 or Brig 35, or an ionic surfactant such as sodium dodecyl sulfate.

EXAMPLES

Figure 1:
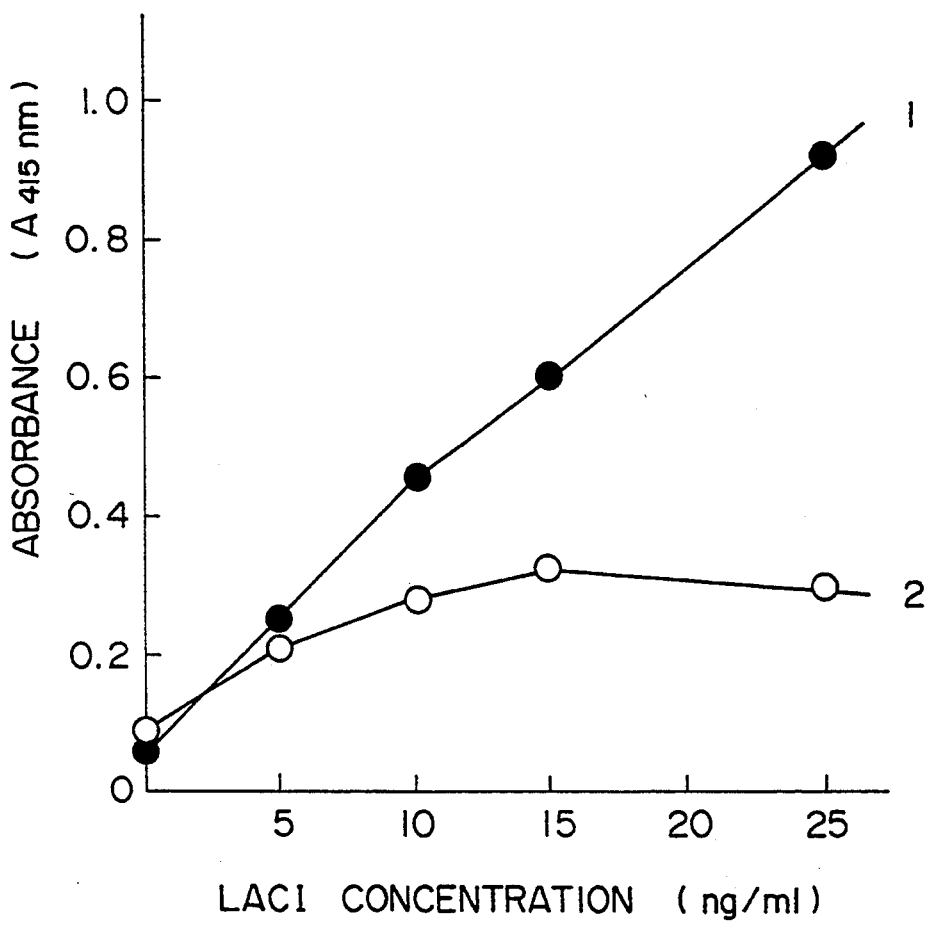
FIG. 1 shows a standard curve for assay of LACI by combination of the K3-antibody and the K1-antibody in this invention. Further, as a comparative example a combination of the K3-antibody and the K2-antibody is also shown.

This invention is described in more detail below by examples. The "%" in examples is based on g/ml (for example, 0.01 g/ml corresponds to 1%).

EXAMPLE 1

Preparation of a Synthetic Polypeptide-Hemocyanin (KLH) Complex 0.3 mg portions of KLH (keyhole limpet hemocyanin) and 1 mg each of the above synthetic polypeptides (K1), (K2) or (K3) were dissolved in 0.5 ml portions of distilled pure water, respectively. To each of the resultant solutions was added 30 mg of EDCI (1-ethyl-3-(3-dimethylaminopropyl)carbodiimide-HCl), and the mixture was subjected to overnight reaction under protection against light at room temperature. The reaction solution was adequately dialyzed against 2 liters of distilled water. Thus was obtained a solution of KLH to which the synthetic peptide bound (concentration: about 0.6 mg/ml). The solution was used as an antigen for immunization.

EXAMPLE 2

Immunization of Mice

On each antigen, immunization was carried out according to the following procedures.

0.5 ml of the solution of KLH to which the synthetic polypeptide bound (0.6 mg/ml) obtained in Example 1 and 0.5 ml of complete Freund's adjuvant were mixed using coupled two injection cylinders, and 0.5 ml portions of the mixture were intraperitoneally administered to two mice, respectively.

Two weeks thereafter, 0.5 ml portions of the mixture were intraperitoneally administered to the mice, respectively. Then four weeks thereafter, 0.5 ml of the solution of KLH to which the synthetic peptide bound (0.6 mg/ml) and 0.5 ml of incomplete Freund's adjuvant were mixed, and the 0.5 ml portions of the mixture were intraperitoneally administered to the mice, respectively. Four weeks thereafter, 50 μl or 100 μl portions of the solution of KLH to which the synthetic peptide bound were intravenously administered to the mice, respectively, three days thereafter the spleen of each mouse was extirpated, and then cell fusion was carried out, as shown in Example 3

EXAMPLE 3

Cell Fusion, and Selection and Obtention of Hybridoma Cells Producing Desired Monoclonal Antibodies, Respectively The extirpated spleen cells of each mouse were mixed with the myeloma cells (P3UI) of the same strain mouse in a ratio of about 6:1, and cell fusion was carried out using 50% polyethylene glycol 1540 as a fusion accelerator. The cells after fusion were suspended in RPMI 1640 medium containing 10% bovine serum so that the cell concentration became $1 \times 10^6$ cells/ml, and 100 μl per well portions of the suspension were put into a 96-well microplate.

The hybridomas (fused cells) were cultured in a $CO_2$ incubator (5% $CO_2$, 37° C.), the medium was replaced by a medium containing hypoxanthine, aminopterin and thymidine (HAT medium), and the hybridomas were proliferated in the HAT medium to screen hybridomas composed of a spleen cell and the myeloma cell. Then, the resultant hybridomas were acclimatized in HAT medium and further acclimatized in 10% FCS-RPMI 1640 medium.

Antibodies in each hybridoma culture supernatant were detected by ELISA method using a microtiter plate on which the aforesaid synthetic peptide was adsorbed. On positive wells, a property to bind to crudely purified LACI was further investigated. Among wells positive in antibody production were selected 8 wells which had exhibited a strong hybridoma proliferation ability and a property to bind strongly to the above synthetic peptide and crudely purified LACI (the first screening). Cloning by a limiting dilution method was carried out two times repeatedly on these wells. Clones having an ability to bind to the peptide and the crudely purified LACI were selected (the second screening). Each of the selected clones was measured for ① the number of cells in the well, ② the concentration of the produced monoclonal antibody obtained by measuring the antibody concentration by ELISA and ③ the amount (absorbance) of the antibody in the well which had bound to the antigen, and clones exhibiting high values on all of ①, ② and ③ were selected (the third screening). It took a little longer than one month in case of K3 antibody or a little shorter than two months in case of the other antibodies to complete the third screening starting from the point of time of the completion of the cell fusion. Each hybridoma stably produced the antibody during this term. From the clones having high performance selected by the third screening were selected representative 4 monoclones having a high antibody production ability and a property to bind strongly to the synthetic peptide and the crudely purified LACI. The obtained clones were suspended in portions of 90% bovine serum solution containing 10% DMSO, and preserved in liquid nitrogen. The monoclonal antibody produced by each clone was obtained by proliferating the clone in the abdominal cavity of a Balb/c mouse and purifying the antibody from ascites using a protein A-Sepharose 4B column.

| | Number of wells at each screening stage | | |
|---|---|---|---|
| | Screening | | |
| Antibody | 1st | 2nd | 3rd |
| K1-antibody | 8 wells | 206 wells | 20 wells |
| K2-antibody | 8 | 161 | 15 |
| K3-antibody | 8 | 237 | 19 |

EXAMPLE 4

Determination of the Classes of the Purified Monoclonal Antibodies (K3-Antibodies)

There was determined according to Ouchterlony's diffusion method the subclass of IgG from each clone purified from the mouse ascites, obtained according to the above Examples 1 to 3 using the synthetic polypeptide (K3). The results were shown in the following Table 1.

TABLE 1

| (Class of K3-antibodies) | | |
|---|---|---|
| Antibody | H chain | L chain |
| 3B1E7 | γ1 | κ |
| 3B1G3 | γ1 | κ |
| 2A1C5 | γ2b | κ |
| 2A1H8 | γ2b | κ |

The epitopes was different from that of 2A1H8 of 2A1C5 and 3B1E7 and 3B1G3 exhibited competitive inhibition. The 2A1 series and the 3B1 series recognized different epitopes.

EXAMPLE 5

Determination of the Classes of the Purified Monoclonal Antibodies (K1-Antibodies)

There was determined according to Ouchterlony's diffusion method the subclass of IgG from each clone purified from the mouse ascites, obtained according to the above Examples 1 to 3 using the synthetic polypeptide (K1). The results were shown in the following Table 2.

TABLE 2

| Antibody | (Class of K1-antibodies) | |
|---|---|---|
| | H chain | L chain |
| 1G1A3 | γ1 | κ |
| 1G1D5 | γ1 | κ |
| 2F2D9 | γ2b | κ |
| 2F2E2 | γ2b | κ |

The 1G1 series and the 2F2 series recognized different epitopes.

EXAMPLE 6

Determination of the Classes of the Purified Monoclonal Antibodies (K2-Antibodies)

There was determined according to Ouchterlony's diffusion method the subclass of IgG from each clone purified from the mouse ascites, obtained according to the above Examples 1 to 3 using the synthetic polypeptide (K2). The results were shown in the following Table 3.

TABLE 3

| Antibody | (Class of K2 antibodies) | |
|---|---|---|
| | H chain | L chain |
| 2G9E9 | γ2b | κ |
| 2G9F1 | γ2b | κ |
| 2G9G8 | γ2b | κ |
| 2C1B1 | γ2b | κ |

2G9E9, 2G9F1 and 2G9G8 recognized the same epitope. The epitope of the 2G9 series was different from that of 2C1B1.

EXAMPLE 7

Detection of Free LACI in the Human Blood by Monoclonal Antibodies

2A1C5, a monoclonal antibody (K3-antibody) recognizing and binding to the third Kunitz site from the N-terminus of LACI, [$Kd = 0.9 \times 10^{-9}$ M], was adsorbed on a microtiter plate (96-cell plate) at a concentration of 20 μg/ml, and then the solid phase was blocked with 20 mM Tris-HCl (pH 7.4) containing 1% BSA and 0.15 M NaCl.

The wells were washed twice with a washing solution (20 mM Tris-HCl (pH 7.4) containing 0.05% Tween 20, 0.5% BSA and 0.15 M NaCl).

In order to draw up a standard curve, LACI was diluted with the washing solution to concentrations of 5, 10, 15 and 25 μg/ml to prepare standard curve solutions, and these solutions were put in the wells, respectively. Separately, human plasmas (normal healthy person and patients) were diluted with the washing solution to 1:5 to prepare specimen solutions, respectively, and they were put in separate wells, respectively. The standard curve solutions and the specimen solutions were subjected to reaction with the monoclonal antibody adsorbed on the plate solid phases, at 37° C. for 2 hours, respectively. After washing, peroxidase-enzyme labeled 2F2D9 [$Kd = 1 \times 10^{-9}$ M] solution (400 ng/ml) was put in each well, and reaction was carried out at 37° C. for 2 hours. Then after washing each well three times with the washing solution, a substrate solution (ABTS) was put in it, and absorbance $A_{415}$ at a wavelength of 415 nm was measured by ELISA ANALYZER (produced by Toyo Sokki Co., Ltd., ETY-96).

The resultant standard curve is shown as curve ① in FIG. 1.

The results on the specimen solutions are shown in the following Table 4.

TABLE 4

| (Free LACI concentration in thrombotic diseases) | |
|---|---|
| Patient of thrombotic diseases | LACI concentration (ng/ml) |
| Pulmonary thrombus | 36 |
| Cardiac venous thrombus | 41 |
| DIC | 73 |
| Normal healthy person (control) | 104 |

It was revealed that in the normal healthy persons (N=5) LACI existed in the blood at a concentration of 104 ng/ml, but in the patients of thrombotic diseases the LACI levels in the plasma were lowered to the order of about $\frac{1}{3} \sim \frac{1}{2}$ compared to the normal healthy persons.

Therefore, detection of the LACI concentration in the plasma is considered to be useful for diagnosis of presence of formation of thrombus in a living body.

EXAMPLE 8

The LACI solutions diluted in the same manner as in Example 7 were reacted with the wells on which a monoclonal antibody, 2A1C5 was adsorbed, shown in Example 7. After washing, was put in the wells a solution (400 ng/ml) of peroxidase enzyme-labeled monoclonal antibody (an antibody recognizing and binding to K2 of the second Kunitz site from the N-terminus of LACI) 2G9F1 (FRI Accession No. FERM BP-4027) [$Kd = 1 \times 10^{-9}$ M], and reaction was carried out at 37° C. for 2 hours. After washing, a substrate solution (ABTS) was added and absorbance was measured. The results were shown in FIG. 1 as curve ②. It was revealed that the combination of the K3-antibody with the K1-antibody had higher assay sensitivity and better quantitative properties than the combination of the K3-antibody with the K2-antibody. In the combination of the K3-antibody with the K2-antibody, it was impossible to assay (quantitatively determine) the LACI concentration in the human plasma. Further in the combination of the K1-antibody with the K2-antibody, assay sensitivity was not raised and it was impossible to detect LACI.

EXAMPLE 9

Distribution of LACI in Tissues in Human Living Bodies

The blood vessel of the placenta of a human being (normal healthy person) was fixated with formalin, embedded with paraffin and sectioned to give a tissue preparation. This tissue was tissue stained with a K3-antibody (2A1C5) and location of LACI was investigated. As a result, it was revealed that LACI was located at the surface of smooth muscle cell in the blood vessel.

Distribution of other tissues was investigated in the same manner as above, and as a result it was revealed that LACI existed in the cardiac muscle and the hepatocyte glycogen area, etc.

EXAMPLE 10

Characteristics of Various Monoclonal Antibodies

Various monoclonal antibodies in various concentrations were added to 200 μl portions of human plasma, respectively, and the mixtures were subjected to reaction at 37° C. for 30 minutes (by this reaction, LACI in the human plasma is bound to the antibodies). Then, 100 μl portions of tissue factor (TF) (concentration: 10 μg/ml) were added, and blood coagulation time was measured using a blood coagulation analyzer (produced by Sysmex Co.). The results are shown in FIG. 2.

Figure 2:
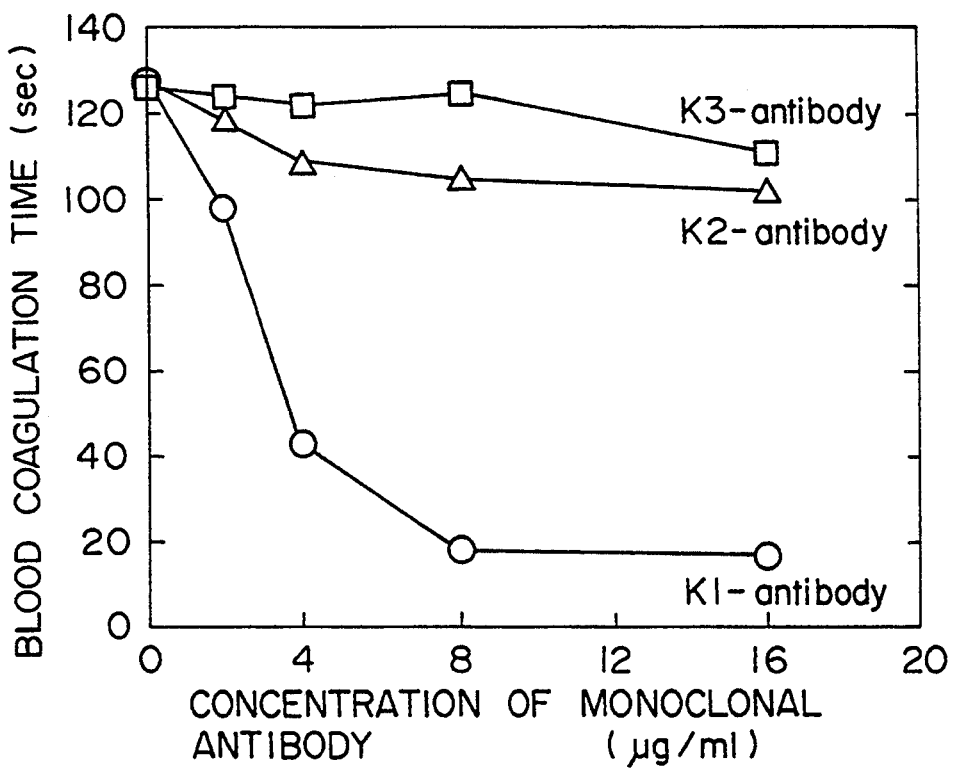
FIG. 2 shows relations between each antibody and blood coagulation time in case of use of various antibodies.

As is seen from FIG. 2, the K1-antibody shortened blood coagulation time with a tendency of concentration dependence. Namely, it was revealed that blocking of the KI site of LACI in the blood with the antibody accelerated blood coagulation. This effect was not observed on the K2-antibody and the K3-antibody.

EXAMPLE 11

Activities of Polypeptides K1, K2 and K3

The synthetic polypeptides shown in Example 1, K1, K2 and K3, were added in various concentrations to 200 μl portions of human plasma, respectively. Then, 100 μl portions of tissue factor (concentration: 50 μg/ml) were added, respectively, and blood coagulation time was measured using a blood coagulation analyzer (produced by Sysmex Co.). The results are shown in FIG. 3.

Figure 3:
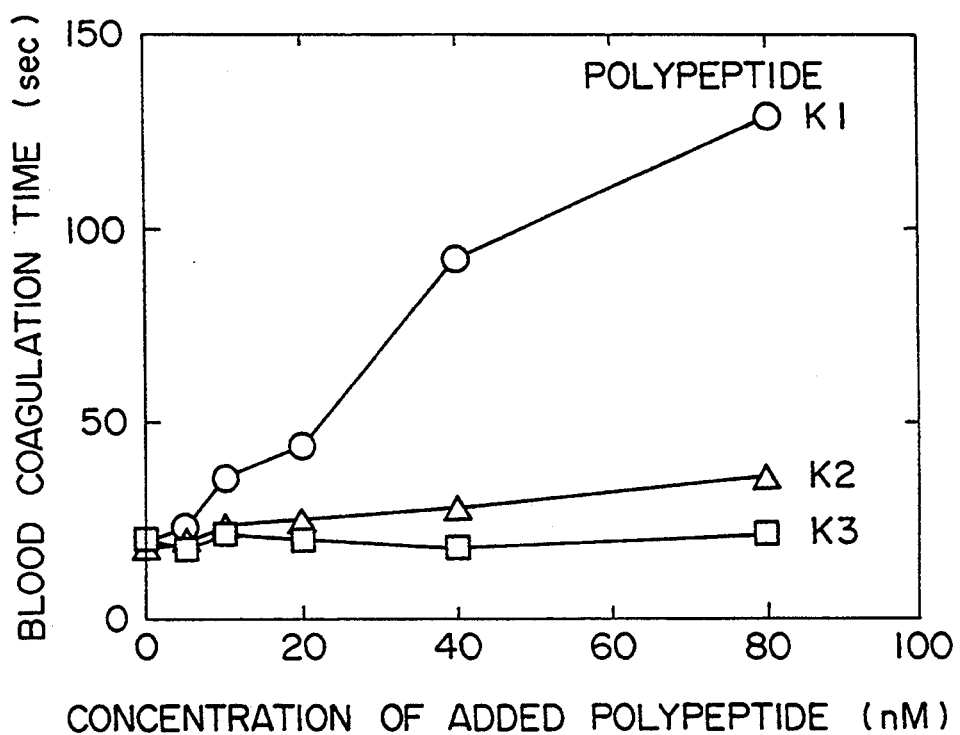
FIG. 3 shows results obtained by investigating blood coagulation time when various synthetic polypeptides were added to plasma and further tissue factor was added.

As is seen from FIG. 3, polypeptide K1 alone has an activity to inhibit thrombus formation specifically, whereas polypeptides K2 and K3 do not have the activity. It is considered from this results that the reactive site is contained in the amino acid sequence of the polypeptide K1 (21 residues).

The "reactive site" is considered to correspond to a TF-VIIa complex inhibiting site in LACI.

Further, when the K2-antibody was reacted with LACI in the blood, the functions of the second Kunitz domain from the N-terminus of LACI reported by Broze et al. (the above-mentioned Nature) remained as they were.

EXAMPLE 12

Effects of Various Monoclonal Antibodies Against the Activity of Polypeptide K1

Polypeptide K1 (40 mM) and various monoclonal antibodies were reacted at 37° C. for 30 minutes, and the resultant reaction mixtures were added to 200 μl portions of human plasma, respectively, 100 μl portions of tissue factor (TF) (concentration: 50 μg/ml) were added, and blood coagulation time was measured using a blood coagulation analyzer (produced by Sysmex Co.). The results are shown in FIG. 4.

Figure 4:
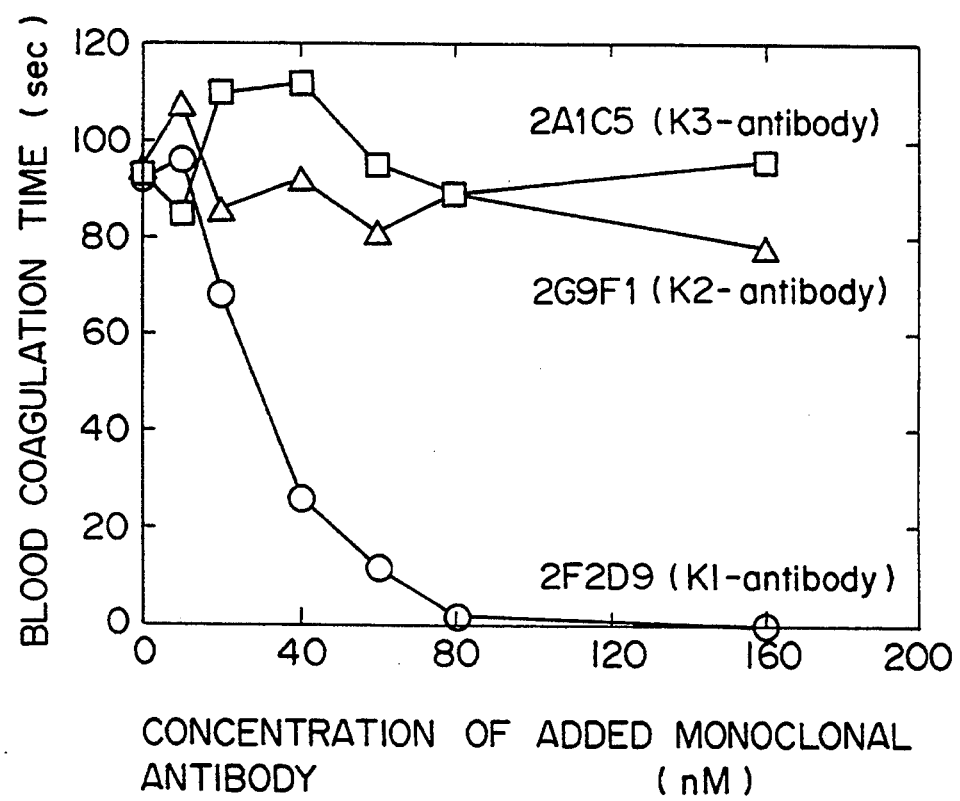
FIG. 4 shows results obtained by investigating the effects of addition of various monoclonal antibodies against the activity of synthetic polypeptide (K1).

As is seen from FIG. 4, a monoclonal antibody 2F2D9 (in a concentration of about 80 nM) recognizing the K1 part of LACI inhibits the thrombus formation inhibitory activity of the K1 peptide.

Effect of the Invention

According to this invention are provided an immunoassay method capable of assaying in high sensitivity free LACI in a human inspection sample and a kit therefor. It is expected that it becomes possible to diagnose the diseases of a patient of a thrombotic disease exactly by accurately assaying free LACI in an inspection sample of the patient in distinction from LACI bound to other proteins. Further, useful monoclonal antibodies used therefor are provided.

We claim:

1. A method for immunologically assaying free lipoprotein associated coagulation inhibitor (hereafter abbreviated as "LACI") in a human sample comprising contacting said sample with a first antibody immobilized on an insoluble carrier and a labeled second antibody, wherein
   (i) any one antibody of the first antibody and the second antibody is a monoclonal antibody which specifically binds to the polypeptide (K3) of the following amino acid sequence (SEQ ID NO:1)

```
Leu Thr Pro Ala Asp Arg Gly Leu Cys Arg
Ala Asn Glu Asn Arg Phe Tyr Tyr Asn Ser
Val
```

(hereafter referred to as a "K3-antibody"), and
   (ii) the other antibody is a monoclonal antibody which specifically binds to the polypeptide (K1) of the following amino acid sequence (SEQ ID NO:2)

```
Ala Phe Lys Ala Asp Asp Gly Pro Cys Lys
Ala Ile Met Lys Arg Phe Phe Phe Asn Ile
Phe
```

(hereafter referred to as a "K1-antibody") to produce a complex consisting of said first antibody, said second antibody and free LACI, and detecting the complex attached to the insoluble carrier.

2. The method of claim 1 wherein the K3-antibody is a monoclonal antibody produced by hybridoma 2A1C5 (FRI Accession No. FERM BP-4017).

3. The method of claim 1 or claim 2 wherein the K1-antibody is a monoclonal antibody produced by hybridoma 2F2D9 (FRI Accession No. FERM BP-4018).

4. The method of claim 1 or claim 2 wherein the first antibody is a K3-antibody and the second antibody is a K1-antibody.

5. A kit for immunologically assaying free LACI in a human sample, which comprises a combination of
   (1) a first antibody immobilized on an insoluble carrier,
   (2) a labeled second antibody,
   (3) a solubilizing agent,
   (4) a washing agent, and wherein
       (i) any one antibody of the first antibody and the second antibody is a K3-antibody according to claim 1, and
       (ii) the other antibody is a K1-antibody according to claim 1.

6. The kit of claim 5, where in said labeled second antibody is labeled with an enzyme and the kit further comprises a substrate specific for said enzyme and a reaction-stopping agent.

7. The kit of claim 5 wherein the K3-antibody is a monoclonal antibody produced by a hybridoma 2a1c5 (FRI Accession No. FERM BP-4017).

8. The kit of claim 5, claim 7 or claim 6 wherein the K1-antibody is a monoclonal antibody produced by hybridoma 2F2D9 (FRI Accession No. FERM BP-4018).

9. The kit of claim 5, claim 7 or claim 6 wherein the first antibody is a K3-antibody and the second antibody is a K1-antibody.

10. A monoclonal antibody which specifically binds to a polypeptide (K3) of the following amino acid sequence (SEQ ID NO:1) Leu Thr Pro Ala Asp Arg Gly Leu Cys Arg Ala Asn Glu Asn Arg Phe Tyr Tyr Asn Ser Val.

11. The monoclonal antibody of claim 10 produced by hybridoma 2A1C5 (FRI Accession No. FERM BP-4017).

* * * * *

SEQUENCE LISTING ( 1 ) GENERAL INFORMATION:

( i i i ) NUMBER OF SEQUENCES: 3

( 2 ) INFORMATION FOR SEQ ID NO:1:

( i ) SEQUENCE CHARACTERISTICS:
        ( A ) LENGTH: 21 amino acids
        ( B ) TYPE: amino acid
        ( C ) STRANDEDNESS: single
        ( D ) TOPOLOGY: linear ( i i ) MOLECULE TYPE:

( i i i ) HYPOTHETICAL:

( i v ) ANTI-SENSE:

( v ) FRAGMENT TYPE:

( v i ) ORIGINAL SOURCE:
        ( A ) ORGANISM:
        ( B ) STRAIN:
        ( C ) INDIVIDUAL ISOLATE:
        ( D ) DEVELOPMENTAL STAGE:
        ( E ) HAPLOTYPE:
        ( F ) TISSUE TYPE:
        ( G ) CELL TYPE:
        ( H ) CELL LINE:
        ( I ) ORGANELLE:

( v i i ) IMMEDIATE SOURCE:

(A) LIBRARY:
                (B) CLONE:

(viii) POSITION IN GENOME:
                (A) CHROMOSOME/SEGMENT:
                (B) MAP POSITION:
                (C) UNITS:

(ix) FEATURE:
                (A) NAME/KEY:
                (B) LOCATION:
                (C) IDENTIFICATION METHOD:
                (D) OTHER INFORMATION:

(x) PUBLICATION INFORMATION:
                (A) AUTHORS:
                (B) TITLE:
                (C) JOURNAL:
                (D) VOLUME:
                (E) ISSUE:
                (F) PAGES:
                (G) DATE:
                (H) DOCUMENT NUMBER:
                (I) FILING DATE:
                (J) PUBLICATION DATE:
                (K) RELEVANT RESIDUES IN SEQ ID NO:

(xi) SEQUENCE DESCRIPTION: SEQ ID NO:1:

Leu Thr Pro Ala Asp Arg Gly Leu Cys Arg
 1           5                       10

Ala Asn Glu Asn Arg Phe Tyr Tyr Asn Ser
                15                   20

Val (2) INFORMATION FOR SEQ ID NO:2:

(i) SEQUENCE CHARACTERISTICS:
                (A) LENGTH: 21 amino acids
                (B) TYPE: amino acid
                (C) STRANDEDNESS: single
                (D) TOPOLOGY: linear (ii) MOLECULE TYPE:

(iii) HYPOTHETICAL:

(iv) ANTI-SENSE:

(v) FRAGMENT TYPE:

(vi) ORIGINAL SOURCE:
                (A) ORGANISM:
                (B) STRAIN:
                (C) INDIVIDUAL ISOLATE:
                (D) DEVELOPMENTAL STAGE:
                (E) HAPLOTYPE:
                (F) TISSUE TYPE:
                (G) CELL TYPE:
                (H) CELL LINE:
                (I) ORGANELLE:

(vii) IMMEDIATE SOURCE:
                (A) LIBRARY:
                (B) CLONE:

(viii) POSITION IN GENOME:
                (A) CHROMOSOME/SEGMENT:
                (B) MAP POSITION:
                (C) UNITS:

(ix) FEATURE:
                (A) NAME/KEY:
                (B) LOCATION:
                (C) IDENTIFICATION METHOD:
                (D) OTHER INFORMATION:

(x) PUBLICATION INFORMATION:
                (A) AUTHORS:

-continued ( B ) TITLE:
    ( C ) JOURNAL:
    ( D ) VOLUME:
    ( E ) ISSUE:
    ( F ) PAGES:
    ( G ) DATE:
    ( H ) DOCUMENT NUMBER:
    ( I ) FILING DATE:
    ( J ) PUBLICATION DATE:
    ( K ) RELEVANT RESIDUES IN SEQ ID NO:

( x i ) SEQUENCE DESCRIPTION: SEQ ID NO:2:

```
Ala  Phe  Lys  Ala  Asp  Asp  Gly  Pro  Cys  Lys
 1              5                        10

Ala  Ile  Met  Lys  Arg  Phe  Phe  Phe  Asn  Ile
               15                        20

Phe
```

( 2 ) INFORMATION FOR SEQ ID NO:3:

( i ) SEQUENCE CHARACTERISTICS:
    ( A ) LENGTH: 21 amino acids
    ( B ) TYPE: amino acid
    ( C ) STRANDEDNESS: single
    ( D ) TOPOLOGY: linear ( i i ) MOLECULE TYPE:

( i i i ) HYPOTHETICAL:

( i v ) ANTI-SENSE:

( v ) FRAGMENT TYPE:

( v i ) ORIGINAL SOURCE:
    ( A ) ORGANISM:
    ( B ) STRAIN:
    ( C ) INDIVIDUAL ISOLATE:
    ( D ) DEVELOPMENTAL STAGE:
    ( E ) HAPLOTYPE:
    ( F ) TISSUE TYPE:
    ( G ) CELL TYPE:
    ( H ) CELL LINE:
    ( I ) ORGANELLE:

( v i i ) IMMEDIATE SOURCE:
    ( A ) LIBRARY:
    ( B ) CLONE:

( v i i i ) POSITION IN GENOME:
    ( A ) CHROMOSOME/SEGMENT:
    ( B ) MAP POSITION:
    ( C ) UNITS:

( i x ) FEATURE:
    ( A ) NAME/KEY:
    ( B ) LOCATION:
    ( C ) IDENTIFICATION METHOD:
    ( D ) OTHER INFORMATION:

( x ) PUBLICATION INFORMATION:
    ( A ) AUTHORS:
    ( B ) TITLE:
    ( C ) JOURNAL:
    ( D ) VOLUME:
    ( E ) ISSUE:
    ( F ) PAGES:
    ( G ) DATE:
    ( H ) DOCUMENT NUMBER:
    ( I ) FILING DATE:
    ( J ) PUBLICATION DATE:
    ( K ) RELEVANT RESIDUES IN SEQ ID NO:

( x i ) SEQUENCE DESCRIPTION: SEQ ID NO:3:

```
Phe  Leu  Glu  Glu  Asp  Pro  Gly  Ile  Cys  Arg
 1              5                        10
```

```
Gly Tyr Ile Thr Arg Tyr Phe Tyr Asn Asn
              15              20
Gln
```